(12) United States Patent
Heinemann et al.

(10) Patent No.: US 12,072,341 B2
(45) Date of Patent: Aug. 27, 2024

(54) FAILURE STATE PREDICTION FOR AUTOMATED ANALYZERS FOR ANALYZING A BIOLOGICAL SAMPLE

(71) Applicant: Roche Diagnostics Operations, Inc., Indianapolis, IN (US)

(72) Inventors: Fabian Heinemann, Munich (DE); Stefan Kobel, Munich (DE); Sven Dahlmanns, Weilheim (DE); Jean-Philippe Vert, Fontainebleu (FR); Yunlong Jiao, Cachan (FR)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1454 days.

(21) Appl. No.: 16/416,844

(22) Filed: May 20, 2019

(65) Prior Publication Data

US 2019/0271713 A1 Sep. 5, 2019

Related U.S. Application Data

(63) Continuation of application No. PCT/EP2017/080518, filed on Nov. 27, 2017.

(30) Foreign Application Priority Data

Dec. 2, 2016 (EP) .................................... 16202003

(51) Int. Cl.
*G01N 35/00* (2006.01)
*G16H 40/40* (2018.01)
*G16H 50/20* (2018.01)

(52) U.S. Cl.
CPC . *G01N 35/00623* (2013.01); *G01N 35/00613* (2013.01); *G01N 35/00693* (2013.01);
(Continued)

(58) Field of Classification Search
None
See application file for complete search history.

(56) References Cited

U.S. PATENT DOCUMENTS 7,050,936 B2 * 5/2006 Levy .................. G06F 11/008
702/179
8,498,776 B2 7/2013 Singh et al.
(Continued)

FOREIGN PATENT DOCUMENTS

CN 1929530 A 3/2007
CN 102073318 A 5/2011
(Continued)

OTHER PUBLICATIONS

Office Action; National Intellectual Property Administration of People's Republic of China; Chinese Application No. 201780073677.X; Oct. 14, 2022; 10 pages.
(Continued)

*Primary Examiner* — Roy Y Yi
(74) *Attorney, Agent, or Firm* — Taft Stettinius & Hollister LLP

(57) ABSTRACT

A method for predicting a failure state of an automated analyzer for analyzing a biological sample is disclosed. The method includes obtaining a prediction algorithm for predicting a failure state of an automated analyzer. The prediction algorithm is configured to predict a failure state of the automated analyzer based on calibration data and/or quality control data generated by an automated analyzer. The method also includes obtaining calibration data and/or quality control data of the automated analyzer and processing the calibration data and/or quality control data by using the prediction algorithm to predict a failure state of the automated analyzer.

20 Claims, 6 Drawing Sheets

(52) U.S. Cl.
CPC ............. *G16H 40/40* (2018.01); *G16H 50/20* (2018.01); *G01N 2035/00633* (2013.01); *G01N 2035/00653* (2013.01)

(56) References Cited

U.S. PATENT DOCUMENTS

| | | |
|---|---|---|
| 2006/0157549 A1 | 7/2006 | Stein |
| 2007/0192078 A1 | 8/2007 | Nasle et al. |
| 2011/0118932 A1 | 5/2011 | Singh et al. |
| 2011/0201121 A1 | 8/2011 | Kaartinen |
| 2012/0042214 A1 | 2/2012 | Jacobs et al. |
| 2012/0191630 A1 | 7/2012 | Breckenridge et al. |
| 2013/0346351 A1 | 12/2013 | Lin et al. |
| 2015/0160098 A1 | 6/2015 | Noda et al. |
| 2015/0378807 A1 | 12/2015 | Ball et al. |
| 2016/0132375 A1* | 5/2016 | Jacobs .................. G16H 40/40 714/47.2 |
| 2016/0146709 A1 | 5/2016 | Dey et al. |

FOREIGN PATENT DOCUMENTS

| | | |
|---|---|---|
| CN | 102129397 A | 7/2011 |
| CN | 103257921 A | 8/2013 |
| CN | 104820747 A | 8/2015 |
| CN | 105447568 A | 3/2016 |
| CN | 105701596 A | 6/2016 |
| EP | 1107159 A2 | 6/2001 |
| EP | 1195681 A2 | 4/2002 |
| EP | 1772736 A1 | 11/2007 |
| EP | 2500731 A2 | 9/2012 |
| EP | 2811300 A1 | 12/2014 |
| JP | 2001-229291 A | 8/2001 |
| JP | 2002-222096 A | 8/2002 |
| WO | 2007048738 A1 | 5/2007 |
| WO | 2010099170 A1 | 9/2010 |

OTHER PUBLICATIONS

Office Action; National Intellectual Property Administration of People's Republic of China; Chinese Application No. 201780073677.X; Mar. 28, 2023; 12 pages.

Office Action; National Intellectual Property Administration of People's Republic of China; Chinese Application No. 201780073677.X; Jun. 21, 2023; 11 pages.

Search Report; National Intellectual Property Administration of People's Republic of China; Chinese Application No. 201780073677.X; Sep. 8, 2023; 3 pages.

European Search Report; The Hague; European Application No. 16202003; May 29, 2017; 2 pages.

* cited by examiner

FAILURE STATE PREDICTION FOR AUTOMATED ANALYZERS FOR ANALYZING A BIOLOGICAL SAMPLE

CROSS-REFERENCE TO RELATED APPLICATIONS

This application is a continuation of PCT/EP2017/080518, filed Nov. 27, 2017, which is based on and claims priority to EP 16202003.6, filed Dec. 2, 2016, which are hereby incorporated by reference.

BACKGROUND

The present disclosure generally relates to systems and methods for predicting a state of an automated analyzer for analyzing biological samples.

Automated analyzers for analyzing biological samples play an important role in today's laboratory environment. In some examples, an automated analyzer such as, for example, a clinical analyzer, may be configured to perform a large number of different and potentially complex tasks. For instance, a clinical analyzer can be set up to carry out a multitude of assays on clinical samples.

Automated analyzers can be fairly costly in terms of purchase and operation. Therefore, optimizing the throughput of an automated analyze is usually of importance. The throughput of an automated analyzer can be severely impaired by downtimes due to the occurrence of unexpected failures (e.g., a sudden breakdown of the analyzer or a module of the analyzer). In some examples, a failure might require that a service technician not readily available at the deployment location of the automated analyzer attend to the automated analyzer (e.g., a service technician travelling to a deployment location of the automated analyzer from a different city or even country). This can result in comparatively extended downtime periods of an automated analyzer.

SUMMARY

According to the present disclosure, a method for predicting a failure state of an automated analyzer for analyzing a biological sample is presented. The method can comprise generating a prediction algorithm for predicting a failure state of an automated analyzer based on historic analyzer data. The historic data can include historic data regarding the occurrence of failure states and historic calibration data and/or quality control data. The prediction algorithm can be configured to predict a failure state of the automated analyzer based on calibration data and/or quality control data generated by an automated analyzer. The method can also comprise obtaining calibration data and/or quality control data of the automated analyzer and processing the calibration data and/or quality control data by using the prediction algorithm to predict a failure state of the automated analyzer.

In accordance with another embodiment of the present disclosure, an automated analyzer for analyzing a biological sample is presented. The automated analyzer can comprise a detection unit to detect one or more properties of a sample, a memory having instructions stored thereon which when carried out on a computer system make the computer system perform the above method, and a processor configured to carry out the instructions stored in the memory.

Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
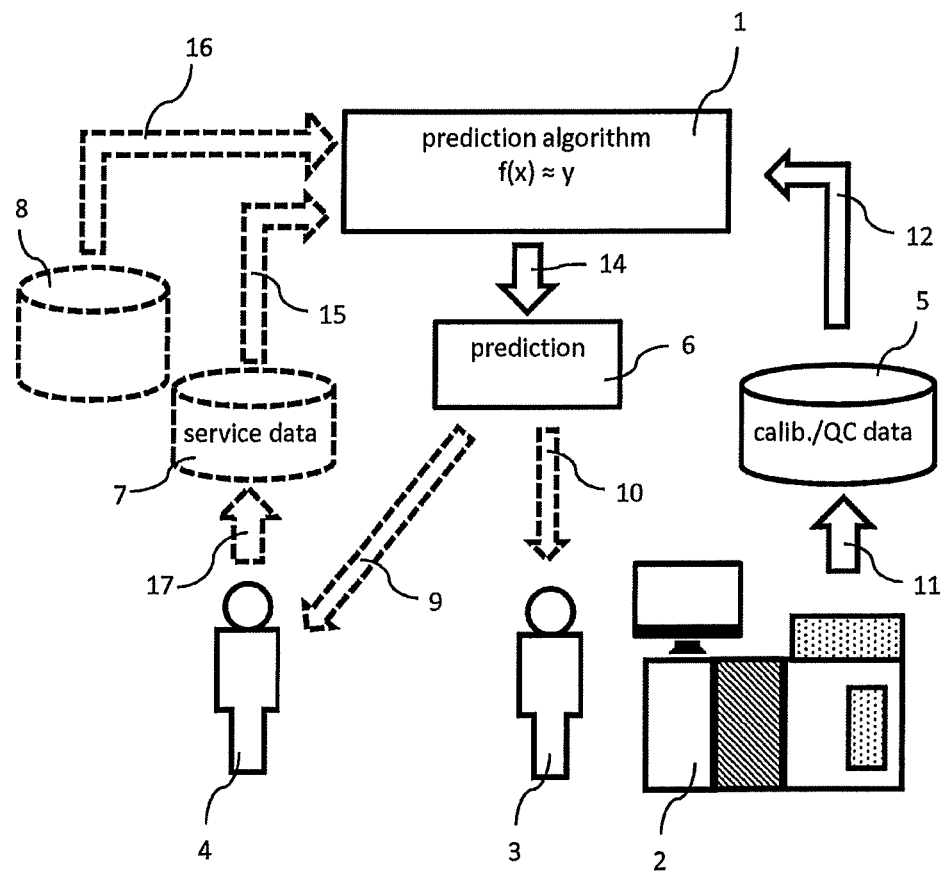
FIG. 1 illustrates a schematic illustration of the data flow in the prediction phase of the method for predicting a state of an automated analyzer according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A method for predicting a failure state of an automated analyzer for analyzing a biological sample is disclosed. The method can include obtaining a prediction algorithm for predicting a failure state of an automated analyzer. The prediction algorithm can be configured to predict a failure state of the automated analyzer based on calibration data and/or quality control data generated by an automated analyzer. The method can also include obtaining calibration data and/or quality control data of the automated analyzer and processing the calibration data and/or quality control data by using the prediction algorithm to predict a failure state of the automated analyzer.

An automated analyzer for samples is also disclosed. The automated analyzer can include a detection unit to detect one or more properties of a sample, a memory having instructions stored thereon which when carried out by a computer system make the computer system perform the above method, and a processor configured to carry out the instructions stored in the memory.

Particular embodiments of the subject-matter of the method and automated analyzer can be implemented so as to realize one or more of the following advantages.

Firstly, the techniques of the present disclosure can allow for predicting a failure state of an automated analyzer. In particular, a failure state may be predicted early enough to leave time to arrange for the appropriate countermeasures in some examples (e.g., contact a service technician to attend to the automated analyzer which may require a lead time of several days). As a result, the downtime of the automated analyzers can be reduced in some examples. In addition, or alternatively, failure state prediction can allow for addressing the cause of the possible failure in a less costly manner in some examples (e.g., without losing samples or with reduced damage to automated analyzer components).

Secondly, the techniques of the present disclosure can allow for prediction surprising failure states in some examples which may not be predictably easily with other monitoring techniques. This can further reduce downtimes of the automated analyzer as surprising failures frequently cause the most substantial downtimes.

Thirdly, the techniques of the present disclosure can be implemented without adding additional or dedicated sensors to the automated analyzers for sensing particular states of the analyzer in some examples. This can be advantageous as additional sensors might increase the complexity of the automated analyzers. In addition, in some examples, regulatory requirements make the addition of sensors to automated analyzers a complicated and costly procedure.

Fourthly, the use of calibration and quality control data to predict a failure state of an automated analyzer can be advantageous as quality control and/or calibration data measurement processes are comparatively well defined in some examples. In this manner, the prediction based on these data items may yield superior prediction results compared to using other data which may be present in the automated analyzer (e.g., measurement data of actual samples).

A number of terms are used in the present disclosure in a particular way:

The term 'analyzer' as used herein can refer to any kind of automated or semi-automated technical device for use in laboratory work, e.g., in the clinical, chemical, biological, immunology or pharmaceutical area or the like used for obtaining a measurement value from a biological sample.

Such a laboratory device may comprise components to perform fluid transfer and dosing, fluid homogenization (mixing), temperature control, and measurements of chemical or physical parameters. For example, the devices can include fluid dispensing components (e.g., a pipettor or a valve), a stirrer, a tempering device, a shaker, or an agitator.

In other examples, automated analyzer can include an analysis system or a work-cell of an analysis system or analyzer. For example, an automated analyzer can be an analyzer for analyzing a mechanical, optical, chemical or biological property of a sample.

'Analyzers' may not necessarily be located in a dedicated laboratory. Rather, the term also can include stand-alone analyzers for carrying out analytic procedures, e.g., in the clinical, chemical, biological, immunology or pharmaceutical area. For example, a benchtop device in point-of-care settings such as physician clinics or pharmacies or a device for home-use can also be automated laboratory equipment according to the present disclosure.

'Analyzers' as used herein can comprise a control unit or controller operatively which can be coupled to one or more analytical, pre- and post-analytical work cells, the control unit being operable to control the work cells. In addition, the control unit may be operable to evaluate and/or process gathered analysis data, to control the loading, storing and/or unloading of samples to and/or from any one of the analyzers, to initialize an analysis or hardware or software operations of the analysis system used for preparing the samples, sample tubes or reagents for the analysis and the like.

The term 'analyzer'/'analytical work cell' as used herein can encompass any apparatus or apparatus component that can measure physical or chemical characteristics of a sample. In some examples, the device can be configured to induce a reaction of a biological sample with a reagent for obtaining a measurement value.

An analyzer can be operable to determine via various chemical, biological, physical, optical or other technical procedures a parameter value of the sample or a component thereof. An analyzer may be operable to measure the parameter of the sample or of at least one analyte and return the obtained measurement value. The list of possible analysis results returned by the analyzer can comprise, without limitation, concentrations of the analyte in the sample, a digital (yes or no) result indicating the existence of the analyte in the sample (corresponding to a concentration above the detection level), optical parameters, images, cell or particle counts, DNA or RNA sequences, data obtained from mass spectroscopy of proteins or metabolites and physical, mechanical, optical, electrical or chemical parameters of various types. An analytical work cell may comprise units assisting with the pipetting, dosing, and mixing of samples and/or reagents. The analyzer may comprise a reagent holding unit for holding reagents to perform the assays. Reagents may be arranged, for example, in the form of containers or cassettes containing individual reagents or group of reagents, placed in appropriate receptacles or positions within a storage compartment or conveyor. It may comprise a consumable feeding unit. The analyzer may comprise a process and detection system whose workflow can be optimized for certain types of analysis.

Examples of such analyzer are clinical chemistry analyzers, coagulation chemistry analyzers, immunochemistry analyzers, urine analyzers, nucleic acid analyzers, used to detect the result of chemical or biological reactions or to monitor the progress of chemical or biological reactions.

The term 'communication network' as used herein can encompass any type of wireless network, such as a WIFI, GSM, UMTS or other wireless digital network or a cable based network, such as Ethernet or the like. In particular, the communication network can implement the Internet protocol (IP). For example, the communication network can comprise a combination of cable-based and wireless networks.

A 'control unit' or 'controller' can control the automated or semi-automated system in a way that the necessary steps for the processing protocols can be conducted by the automated system. That can mean the control unit may, for example, instruct the automated system to conduct certain pipetting steps to mix the liquid biological sample with reagents, or the control unit controls the automated system to incubate the sample mixtures for a certain time and the like. The control unit may receive information from a data management unit regarding which steps need to be performed with a certain sample. In some embodiments, the control unit may be integral with the data management unit or may be embodied by a common hardware. The control unit may, for instance, be embodied as a programmable logic controller running a computer-readable program provided with instructions to perform operations in accordance with a process operation plan. The control unit may be set up to control, for example, any one or more of the following operations: loading and/or wasting and/or washing of cuvettes and/or pipette tips, moving and/or opening of sample tubes and reagent cassettes, pipetting of samples and/or reagents, mixing of samples and/or reagents, washing pipetting needles or tips, washing mixing paddles, controlling of a light source, e.g., selection of the wavelength, or the like. In particular, the control unit may include a scheduler, for executing a sequence of steps within a predefined cycle time. The control unit may further determine the order of samples to be processed according to the assay type, urgency, and the like.

The term 'biological sample' can refer to material(s) that may potentially be contain an analyte of interest. The sample can be derived from a biological source, such as a physiological fluid, including blood, saliva, ocular lens fluid, cerebrospinal fluid, sweat, urine, stool, semen, milk, ascites fluid, mucous, synovial fluid, peritoneal fluid, amniotic fluid, tissue, cells, or the like. The biological sample can be pretreated prior to use, such as preparing plasma or serum from blood. Methods of treatment can involve centrifugation, filtration, distillation, dilution, concentration and/or separation of sample components including analytes of interest, inactivation of interfering components, and the addition of reagents.

A sample may be used directly as obtained from the source or used following a pretreatment to modify the character of the sample. In some embodiments, an initially solid or semi-solid biological material can be rendered liquid by dissolving or suspending it with a suitable liquid medium. In some examples, the sample can be suspected to contain a certain antigen or nucleic acid.

A sample can be treated before analytical testing is done. Blood sampled from a patient can, for example, be centrifuged to obtain serum or treated with anti-coagulants to obtain plasma.

The term 'quality control data' as used in the present disclosure can refer to the result of a measurement by an automated analyzer of a quality control. A 'quality control' according to the present disclosure can include one or more control materials with known target measurement values to be output by the automated analyzer. The measurement procedure on the quality control can be a check that the automated analyzer operates within a predetermined limit of accuracy and/or precision. In other words, a 'quality control' can be used in the present disclosure as referring to a physical sample used in one or several monitoring processes to monitor the performance of particular tests or assays of the analyzer.

For instance, such test or assay can be a determination of a thrombin clotting time in which the time it takes is measured for a clot to form in the plasma of a blood sample containing anticoagulant after an excess of thrombin has been added. In this test, a quality control can include blood plasma as a first quality control ingredient (matrix) and thrombin as a second quality control ingredient.

The same particular quality control can be used to monitor the performance of a plurality of tests or assays of an analyzer in some examples. On the other hand, monitoring the performance of a particular test or assay of any analyzer may include different types of quality controls.

A quality control can include one or more quality control ingredients. The term 'quality control ingredient' can include any substance that can be a constituent of a quality control to be used to monitor the performance of a particular test of an automated analyzer.

In one example, quality control ingredients can include a matrix (e.g., a matrix solution). These matrices can be derived from a bodily fluid or a constituent of a bodily fluid. In other examples, the matrix (e.g., matrix solution) can be an artificial substance which mimics properties of a bodily fluid or of a constituent of a bodily fluid. In some examples, the matrix (e.g., matrix solution) can include blood, saliva, ocular lens fluid, cerebrospinal fluid, sweat, urine, stool, semen, milk, ascites fluid, mucous, synovial fluid, peritoneal fluid, amniotic fluid, tissue, cultured cells, or constituents of these bodily substances. In other examples, the matrix can include a concentrated or diluted form of these bodily substances. In one example, a matrix solution can be blood plasma or blood serum. In one example, the matrix solution can be freeze-dried. In one example, only the matrix solution among the quality control ingredients is freeze-dried.

In addition, or alternatively, quality control ingredients can include modifying agents (also referenced as 'modifiers' in the present disclosure). In some examples, a modifying agent can include one or more of a drug, a metabolite of a drug, a substance that accumulates in a predetermined medical or metabolic condition, a substance that is normally not present in a bodily fluid, and a substance that is normally present in a bodily fluid.

In addition, or alternatively, quality control ingredients can include reagents. The term 'reagent' can refer to a substance which is added to a biological sample when performing a particular test on the biological sample in the analyzer to elicit a particular reaction in the blood sample. The reagents can be specific for a particular test or assay. For example, in a situation where a partial thromboplastin time of a blood sample can be determined, the analyzer can be configured to add an activator as reagent to the blood sample to activate the intrinsic pathway of coagulation. Particular substances can be 'modifying agents' or 'reagents' according to the present disclosure in different situations. In some examples, an analyzer may not add a reagent to a biological sample to be analyzed. Accordingly, a quality control may not include a reagent in some examples.

In the present disclosure, 'calibration data' can include data from measurements in which a response signal to one or more standard calibrators having a known composition is determined by the analyzer to generate a relationship between the response signal and the known composition. This relationship can then be used to set the measurement range of the automated analyzer. For example, in a device detecting an absorption value of a sample, a standard calibrator can include a sample having a known absorption value. In response to the calibration measurement, the automated analyzer can be calibrated so that it indicates the true absorption value (or at least a value coming close to the true value within a predetermined limit) in an absorption measurement.

The term "failure state" as used herein can relate to a state of an analyzer indicative of one or more of the list comprising (but not limited to): broken or worn components of the analyzer such as actuators (motors), valves, sensors or other hardware (tubings, springs, screws or any other parts of an analyzer). The term failure state can further relate to indication of one or more of: bad adjustments/settings, leakages in the fluidic path of an instrument, corrosion, broken or defective electronics, and the like. In particular, failure state can be indicative of a software, hardware failure or miss-configuration thereof which affects analysis of biological sample(s).

The methods and systems for predicting a failure state of an automated analyzer according to the present disclosure will subsequently be discussed in more detail.

First, the operations which may take place in the prediction phase when the prediction algorithm is applied to predict a failure state will be illustrated in connection with FIG. 1 and FIG. 5. Subsequently, aspects of the data used in the techniques of the present disclosure will be discussed in connection with FIG. 2. Next, the generation phase and training phase of a prediction algorithm according to the present disclosure will be explained in more detail in connection with FIG. 3 and FIG. 5. In connection with FIG. 4, additional aspects of the prediction algorithm will be discussed. Last, a concrete example for using the techniques of the present disclosure will be given in connection with FIG. 6a and FIG. 6b.

Applying the Prediction Algorithm

FIG. 1 illustrates the data flow in an example method for predicting a failure state of an automated analyzer 2 for samples. FIG. 5 illustrates method steps performed during application of the prediction algorithm.

The method can include obtaining 201 a prediction algorithm 1 for predicting a failure state of an automated analyzer 2, the prediction algorithm 1 can be configured to predict a failure state of the automated analyzer 2 based on calibration data and/or quality control data 5 generated by an automated analyzer. Furthermore, the method can include obtaining 11, 202 calibration data and/or quality control data 5 of the automated analyzer 2 and processing 14, 203 the calibration data and/or quality control data by using the prediction algorithm 1 to predict a failure state of the automated analyzer 2.

These operations and additional operations which may take place in the prediction phase according to the present disclosure will be discussed in more detailed in the subsequent sections below.

The automated analyzer 2 can be any of the automated analyzers discussed above. In the subsequent sections, a clinical analyzer is occasionally used as an example automated analyzer. However, the techniques presented subsequently can also be applied to any of the other automated analyzers listed above (unless a specific feature of the respective technique is incompatible with the particular type of analyzer).

The prediction algorithm 1 can be obtained in one of several ways. In one example, the prediction algorithm 1 can be stored for subsequent use in the memory of the automated analyzer 2. For example, the prediction algorithm 1 can be stored for use in a local memory of the automated analyzer 2.

However, in other examples, the prediction algorithm 1 can be stored in a memory remote from the automated analyzer 2 which can be networked with the automated analyzer 2 by a communication network. For instance, the prediction algorithm 1 can be stored in a laboratory information system or a hospital information system. In still other examples, the prediction algorithm 1 can be stored in a remote or distributed location such as, for example, a remote server or the cloud.

In any case, the prediction algorithm 1 can be arranged to access calibration data and/or quality control data 5 of the automated analyzer 2.

In some examples, the prediction algorithm 1 can be installed on the automated analyzer 2 in a setup process of the automated analyzer 2 (e.g., as part of a factory setup of the automated analyzer). In other examples, the prediction algorithm 1 can be obtained (e.g., installed on the automated analyzer) during operation of the automated analyzer 2 (e.g., downloaded through a communication network).

In general, the term 'prediction algorithm' in the present disclosure can refer in an abstract manner to an entity which can be configured to process calibration data and/or quality control data to make a prediction regarding the state of the automated analyzer. The prediction algorithm may be embodied in hardware, software or any combination thereof. In one example, the prediction algorithm can be included in a control software of the automated analyzer so that the automated analyzer can use the prediction algorithm in a similar manner as other functions of the control software. It can be understood that the concrete implementation of the prediction algorithm is immaterial for the operation of the prediction algorithm.

In the example of FIG. 1, the prediction algorithm is illustrated as a function which processes an input ("x") and yields an output ("y"). In the following sections, the input can include the calibration data and/or quality control data and the output can include a prediction whether a failure state is to be expected within a predetermined time. However, as will be discussed below, the prediction algorithm can have other forms, can be adapted to process other data or to yield other results in other examples.

Coming back to FIG. 1, an operator 3 can operate the automated analyzer 2 during "normal" operation of the automated analyzer 2. In particular, the operator 3 can carry out calibration procedures and/or quality control procedures (also referred to as 'calibration operations and/or quality control operations' or 'calibration routines and/or quality control routines' in the present disclosure). In the course of these procedures, the automated analyzer 2 can generate 11 calibration data and/or quality control data 5. In other examples, the automated analyzer 2 can carry out the calibration procedures and/or quality control procedures (at least partially) automatically.

A quality control procedure can include determining of a response signal of the automated analyzer 2 to one or more one or more control materials with known target measurement values, checking that the automated analyzer 2 operates within a predetermined limit of accuracy and/or precision and including results of the checking step in the quality control data 5; 5a.

A calibration procedure can include determining of a response signal of the automated analyzer 2 to one or more standard calibrators having a known composition, generate a relationship between the response signal and the known composition and including the relationship into the calibration data 5; 5a.

In some examples, the operator 3 may carry out a quality control procedure for a particular assay installed on the clinical analyzer 2 at predetermined times (e.g., at the start and the end of a predetermined period of time in which the particular assay is carried out on the clinical analyzer). In some examples, this technique can be applied to validate a number of measurements for this particular assay taking place between the subsequent quality control procedures.

In other examples, the operator 3 may carry out a calibration measurement to calibrate a particular measurement function of the clinical analyzer 2 (e.g., at predetermined date or after a predetermined number of assays have been performed by the automated analyzer).

In both cases, the procedures may include the use of well-defined calibration or quality control standards. Examples of calibration or quality control samples are discussed above.

The calibration data and/or quality control data 5 can then be used by the automated analyzer 2 for calibration and/or quality control purposes. In addition, the calibration data and/or quality control data 5 can be provided 12 to the prediction algorithm for processing to predict a failure state of the automated analyzer 2.

Therefore, the prediction algorithm may use only data which is in any case obtained during operation of the clinical analyzer 2 in some examples. In other examples, the prediction algorithm 1 may also process other data.

For example, the prediction algorithm may process other instrument data of the automated analyzer 1 in addition to the calibration and/or quality control data. This can include one or more of data obtained when carrying out measurements on samples (e.g., transmission or absorption measurement or other optical measurements), data obtained from sensors of the automated analyzer 1 (e.g., temperature sensors or moisture sensors, or other sensors monitoring the automated analyzer environment) and control data generated during operation of the automated analyzer 1.

In addition, or alternatively, data from dedicated sensors to monitor or a proper operation of the automated analyzer can be used by the prediction algorithm 1. However, in other examples, the use of this type of dedicated sensors can be avoided when using the techniques of the present disclosure.

The calibration data and/or quality control data 5 can then be processed 14 by the prediction algorithm 1 to obtain a prediction 6 regarding a failure state of the automated analyzer 2. Details regarding the way how the prediction algorithm 1 processes the calibration data and/or quality data 5 will be discussed below. In the subsequent sections, different possible prediction results and how they can be used will be discussed in more detail.

In one example, the prediction 6 regarding a failure state of the automated analyzer can include a prediction that a predetermined type of error (or one of a predetermined set of errors) is likely to occur. In one example, the prediction 6 can include a specification of the time window in which the failure state is likely to occur or a time when the failure state is likely to occur, or both.

The predetermined type of error (or set of errors) can include an error which requires that service technician 4 attends to the automated analyzer 2. Other types of failures will be discussed below in connection with FIG. 2.

Regardless of the type of the prediction, the prediction can be used in different ways in the techniques of the present disclosure. Different examples will be discussed in the subsequent paragraphs.

In one example, the result of processing the calibration data and/or quality control data 5 and determining a prediction 6 of a failure state can be communicated 9 to a service technician 4 (or any other person, group or entity responsible for servicing the automated analyzer 2). For instance, the service technician (or other person, group or entity responsible servicing the automated analyzer 2) can be located remotely from the location of the automated analyzer 2. For example, the service technician may receive a warning message including the prediction 6 of the prediction algorithm 1 regarding a future failure state of the automated analyzer 2. In this manner, the service technician 4 can receive the prediction of the failure state of the automated analyzer 2 with enough lead time to a possible failure to attend to the automated analyzer 2 before the failure is likely to occur.

In some examples, communication with a service technician 4 (or other entity responsible for servicing the automated analyzer 2) can only take place if the prediction algorithm 1 predicts the occurrence of a failure state. In other examples, communication with the service technician 4 (or other entity responsible servicing the automated analyzer 2) can only take place if the prediction algorithm 1 predicts occurrence of failure state with a predetermined threshold likelihood. In still other examples, all prediction data produced by the prediction algorithm 1 can be communicated to a service technician 4. The communication of the prediction 6 may occur automatically in some examples.

In addition, or alternatively, the prediction 6 of the prediction algorithm 1 can be communicated 10 to an operator 3 of the automated analyzer 2. In other examples, the prediction 6 of the prediction algorithm 1 can be communicated to other personnel or devices located in the environment of the automated analyzer 2.

For example, a warning or information message can be produced and circulated in a network environment including the automated analyzer 2 (e.g., a laboratory or hospital network). In addition, or alternatively, a warning or information message can be output on a display device of the automated analyzer 2, or on a display of a device networked with the automated analyzer 2.

Again, the prediction 6 may only be communicated if a failure state of the automated analyzer 2 is predicted, or if a possibility that a failure state of the automated analyzer 2 occurs is predicted to be higher than a predefined threshold. In this manner, countermeasures can be initiated to avoid the failure state of the automated analyzers 2, or at least ameliorate the consequences of the occurrence of failure state in some examples.

In the preceding sections, multiple examples of using the prediction algorithm according to the present disclosure have been discussed. Subsequently, in connection with FIG. 2, additional explanations regarding how the calibration data and/or quality control data of the automated analyzer is used will be given.

Figure 2:
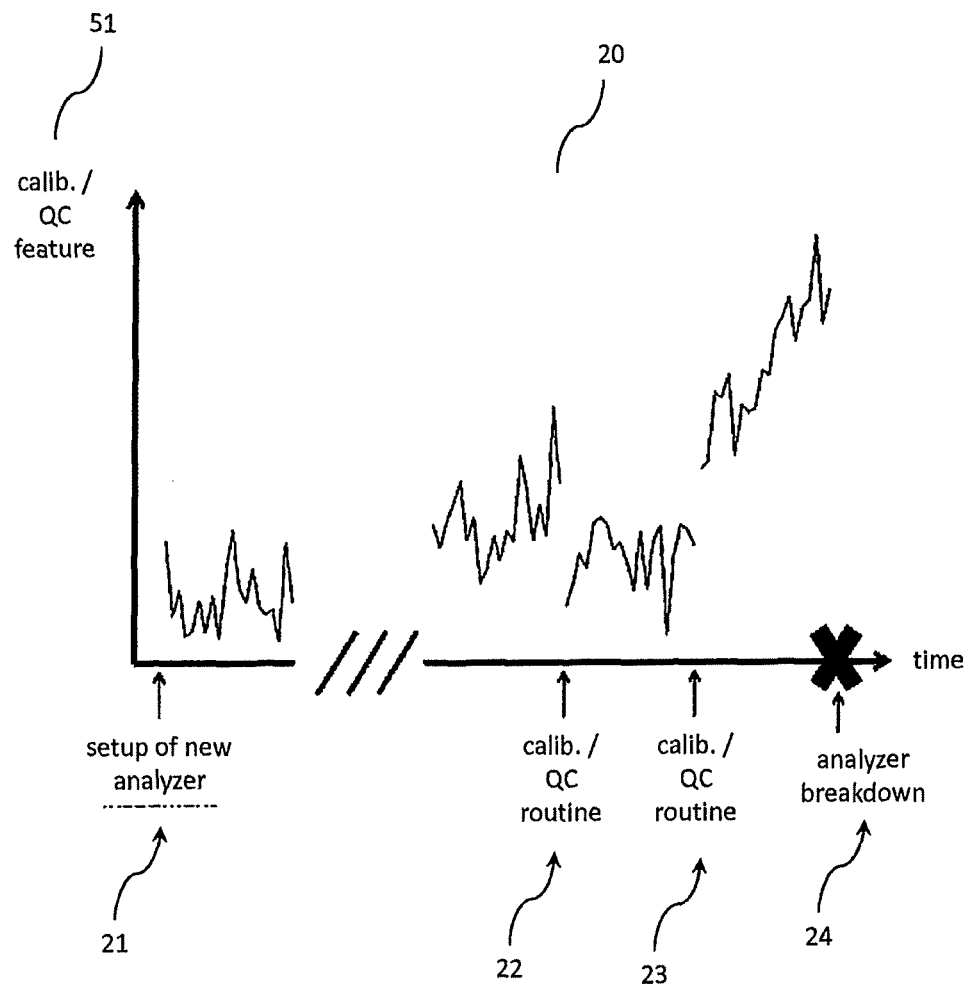
FIG. 2 illustrates a graph of an example calibration data or quality control data related feature and different events taking place during operating of an automated analyzer according to an embodiment of the present disclosure.

FIG. 2 includes a graph 20 of an example calibration data and/or quality control data related feature 51 and different events 21-24 taking place while operating an automated analyzer.

As can be seen in FIG. 2, the calibration data and/or quality control data can include a scalar parameter which varies over time. At a first time, the automated analyzer can be set up 21. In the course of the lifetime of the automated analyzer, calibration and/or quality control routines 22, 23 can be performed (e.g., as discussed above). At some time, an unexpected failure of the analyzer occurs (referenced as "analyzer breakdown" in FIG. 2). As can be seen in the example graph 20, the parameter of the calibration data and/or quality control data can rise significantly in the period of time preceding the failure of the automated analyzer. The techniques of the present disclosure may exploit this behavior to predict the failure state of the automated analyzer (a predetermined time in advance in some examples). In other words, the calibration data and/or quality control data may have a predictive power for certain failure states of the automated analyzer in some examples.

In the example of FIG. 2, a scalar parameter included in the calibration data and/or quality control data has been used for the sake of illustration. In other examples, the calibration data and/or quality control data can have one or more of the characteristics listed in the subsequent paragraphs.

For example, the calibration data and/or quality control data can include a frequency data of calibration events or quality control events (e.g., the frequency with which calibration routines and/or quality control routines are performed).

In addition, or alternatively, the calibration data and/or quality control data can include distribution information of signals measured during calibration events or quality control events. The distribution information can include one or more of average values (e.g., an arithmetic average or median), variation values (e.g., a standard variation, spread, quantile information or other value characterizing a variation) of signals measured during calibration events or quality control events.

For example, the calibration data and/or quality control data can include an arithmetic average of signals measured during calibration events or quality control events. In other examples, the calibration data and/or quality control data can include a standard variation of signals measured during calibration events or quality control events (or another measure quantifying measurement noise).

In addition, or alternatively, the calibration data and/or quality control data can include data regarding changes of signals measured during calibration events or quality control events. In other examples, the calibration data and/or quality control data can include information obtained from a derivation of signals measured during quality control and calibration events (or a higher order derivation of the signals measured during calibration events or quality control events).

In still other examples, the calibration data and/or quality control data can be processed into expressions combining multiple different items of calibration data and/or quality control data to be processed by the prediction algorithm. For example, different items of calibration data and/or quality control data can be processed to obtain, e.g., weighted sums, ratios, or other combined expressions.

In the example of FIG. 2, the failure state of the automated analyzer can be an analyzer breakdown. However, different failure states can be predicted with the prediction techniques of the present disclosure (e.g., the failure states discussed above).

For example, the prediction techniques of the present disclosure may be adapted to predict failures in different components of an automated analyzer. In addition, or alternatively, the prediction techniques of the present disclosure may be adapted to predict failures in different functions the automated analyzer can perform (e.g., a failure in performing a predetermined assay or group of assays).

In still other examples, the prediction techniques of the present disclosure can be configured to predict failure states having a predetermined severity. For example, a failure state can be a failure state requiring an emergency service with a visit at the automated analyzer. In addition, or alternatively, a failure state can be a failure state requiring that can be resolved by a remote service.

In other examples, a failure state can be a state in which the particular operation is to be performed on the automated analyzer to secure proper operation of the automated analyzer.

In still other examples, the type of error can be an error which requires a particular spare or replacement part to replace a component of the automated analyzer. For example, a failure state may include the end of life of a particular component of the automated analyzer (e.g., a dispensing device or an illumination device).

In the example of FIG. 2, a failure state can refer to a "catastrophic event." However, in other examples, the techniques of the present disclosure can be used to predict more common events in the lifecycle of an automated analyzer. For example, a failure state may involve any state in which the automated analyzer is not operating within a predefined limit. In one example, a component of the automated analyzer may reach its end of life or approach a service event. For instance, a lamp of an illumination unit may reach its end of life.

In one example, a dispensing device of the automated analyzer may gradually clog with time. As a result, at some point in time, the dispensing device may not dispense an appropriate amount of fluid anymore. This point in time can be a failure state as the automated analyzer may not be properly operating if the dispensing device is clogged to that degree. The techniques of the present disclosure can be used to predict a failure state. As a result, an operator of the automated analyzer can intervene timely enough to avoid negative consequences of the occurrence of the failure state. For example, if the dispensing device ceases to operate properly during operation of the automated analyzer, it may be the case that incorrect results are obtained and/or samples are spoiled or lost in the process. These negative consequences can be avoided when using the prediction techniques of the present disclosure in some examples.

Generating and Training the Prediction Algorithm

In connection with FIG. 1 and FIG. 2 above, different aspects regarding the use of the prediction algorithm of the present disclosure have been discussed. In the following sections, in connection with FIG. 3 and FIG. 5, additional details regarding the types of prediction algorithms that can be employed and details regarding the generation of the prediction algorithms will be discussed in more detail.

Figure 3:
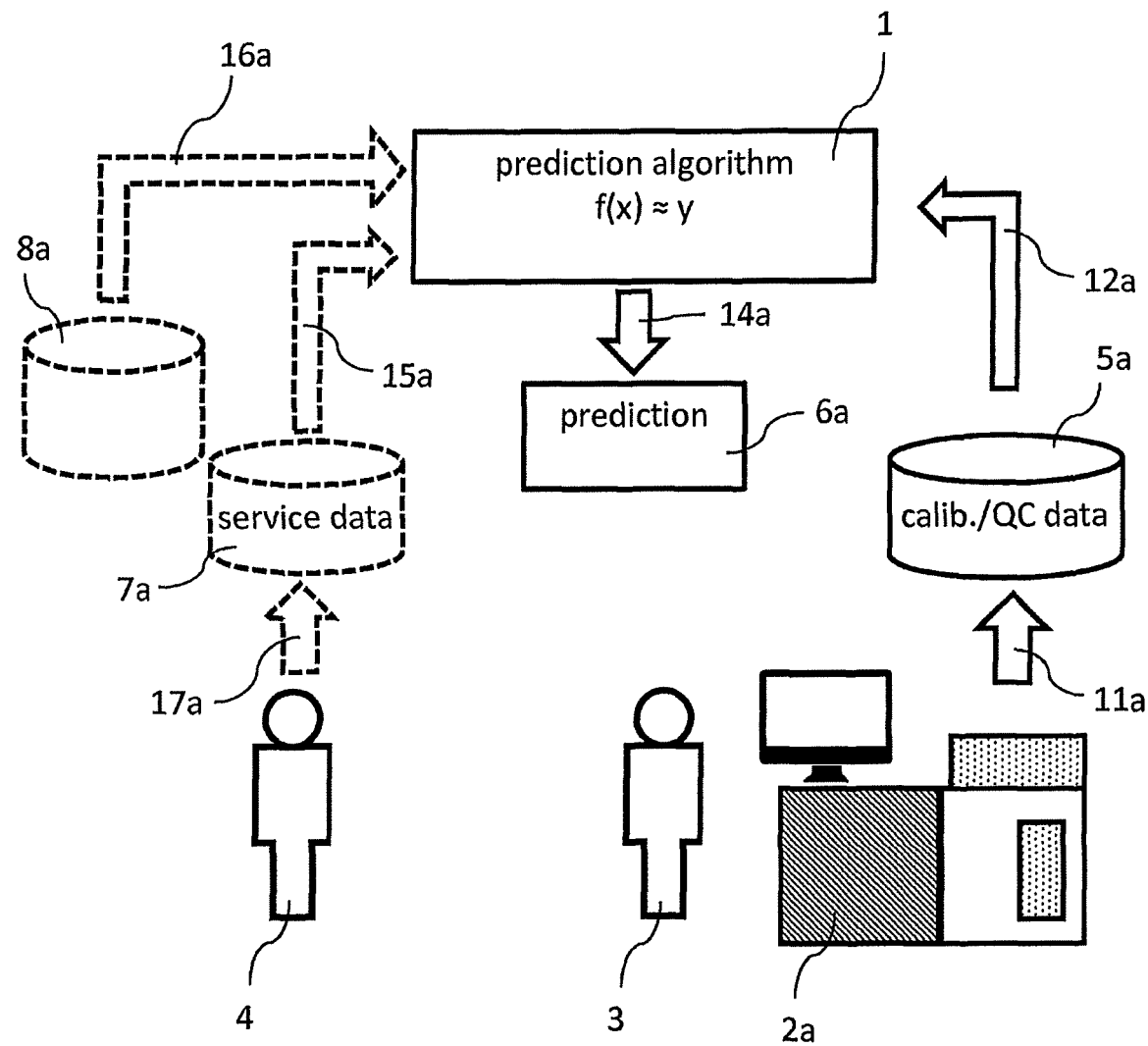
FIG. 3 illustrates a schematic illustration of the data flow in the training phase of the method for predicting a state of an automated analyzer according to an embodiment of the present disclosure.

FIG. 3 includes a schematic illustration of the data flow in the training phase of the method for predicting a state of an automated analyzer 2a according to the present disclosure.

In general, during a generation and training phase of the prediction algorithm 1, historic automated analyzer data can be used to generate and train 301 the prediction algorithm 1. In particular, the historic analyzer data can include historic calibration data and/or quality control data 5a and historic data regarding the occurrence of failure states 7a, 8a.

The generation and training phase may include different steps. In one example, an initial prediction model can be tuned and refined by using the historic data (e.g., one or more parameters of the model are set). In other examples, the generation and training phase can also include setting up the prediction algorithm from scratch (e.g., selecting a type of classifier and the historic data to be used).

In the present disclosure, the term 'historic' can be used to distinguish the calibration data and/or quality control data (or any other data) used in the training phase of the prediction algorithm 1 and the calibration data and/or quality control data (or any other data) used when applying the prediction algorithm 1 to predict a failure state of an automated analyzer. Therefore, the term 'historic data' can refer to data collected in the past as seen from a point in time when the prediction algorithm is applied to predict a failure state of the automated analyzer. This can mean that in a training phase of the prediction algorithm, the calibration and/or quality control data (or any other data) not necessary can be data collected in the past. In addition, the term 'historic' is not intended to convey any particular remoteness in time. For instance, historic data may be collected just a couple of minutes or seconds before a present time in which the prediction algorithm is applied.

Having said this, the historic data used to generate and train the prediction algorithm can include the same type of data discussed above in connection with using the prediction algorithm to predict a failure state of the automated analyzer. In particular, the historic data can include (at least partially) the same type of calibration data and/or quality control data which can also be produced by the automated analyzer in operation.

Moreover, the generation and training phase can include using data regarding the occurrence of failure states of the automated analyzer 7a, 8a. In one example, the data regarding the occurrence of failure states can include service data of automated analyzers 7a. For instance, the service data can include data retrieved from reports by a service technician (or any other person entrusted with servicing the automated analyzer).

In one example, the service data 7a can include one or more of an automated analyzer ID, a visit date (or any other time stamp) of a service technician, component consumption information and descriptions of the activities performed on the automated analyzer. In general, the service data 7a can include data timing the occurrence of a failure state.

In addition, or alternatively, the historic data regarding the occurrence of failure states can include information regarding errors generated by an automated analyzer itself. For instance, the automated analyzer may generate error messages or internal logs of failure states. For instance, the automated analyzer may detect that the particular component or a particular function is no longer operating properly (e.g., a quantity of liquid dispensed by a predetermined dispensing device is insufficient). This event may be recorded or a corresponding error message can be generated by the automated analyzer.

In general, the data regarding the occurrence of failure states can include any information regarding the occurrence of a failure state of the automated analyzer. For example, the data regarding the occurrence of failure states may also be generated by the use of additional sensors or detectors, or by visual inspection by an operator during the training phase.

The data regarding the occurrence of failure states can also include data confirming the proper operation of the automated analyzer 8a. In other words, the data regarding the occurrence of failure states can include information that no failure has occurred (e.g., within a predetermined period of time). For example, this information can be a binary information that no failure has occurred, or information indicating that the automated analyzer 2a is operating within the predefined limits.

In the training phase, the prediction algorithm 1 can be provided 12a, 15a, 16a with the data described above which can be processed 14a by the prediction algorithm 1 to make a prediction 6a regarding a failure state of the automated analyzer 2a. In the generation and training phase, this prediction 6a can be compared with the actually occurring failure state of the automated analyzer 2a. In this manner, the quality of the prediction 6a can be determined and the prediction algorithm 1 can be modified and tuned in reply to this assessment.

The prediction algorithm 1 can be selected and trained to predict failure states of the automated analyzer 2a with a certain degree of certainty (e.g., the predictive power of the production algorithm 1 can be optimized in the generation and training phase). In other examples, the production algorithm 1 can be selected and trained to reduce a number of false alerts, or a combination of predicting failure states of the automated analyzer 2a with a certain degree of certainty and reducing a number of false alerts.

In some examples, selecting the prediction algorithm 1 can include finding a relationship between the historic data regarding the occurrence of failure states 7a, 8a and the historic calibration data and/or quality control data 5a. For example, selecting the prediction algorithm 1 can include correlating the historic data regarding the occurrence of failure states 7a, 8a and the historic calibration data and/or quality control data 5a.

For instance, this process can involve using a classification technique on the historic data regarding the occurrence of failure states 7a, 8a and the historic calibration data and/or quality control data to find the relationship 5a.

Example classification techniques that can be used to select the prediction algorithm 1 according to the present disclosure can involve one or more of a technique including using a decision tree, a technique using a support vector machine, a random forest machine learning algorithm, a deep learning algorithm, a logistic regression technique, a (naïve) Bayes technique, a gradient boosting technique or linear discriminant analysis.

In the examples below, a technique including using a decision tree is employed. While this technique can have particular advantages in some examples, the techniques of the present disclosure are not limited in that respect. For example, the historic calibration and/or quality control data and the historic data regarding occurrence of failure states described in the present disclosure can also be used in a deep learning procedure (e.g., to train a neural network to predict a failure state of an automated analyzer). In still other examples, the historic calibration and/or quality control data and the historic data regarding occurrence of failure states described in the present disclosure can be used to set up and train a support vector machine. Other classifiers and predicting techniques can be applied accordingly.

After the generation of the prediction algorithm, the prediction algorithm can be provided 302 to an automated analyzer to predict a failure state of the automated analyzer (as discussed in connection with FIG. 1 above).

An example technique to generate and train a prediction algorithm 1 will subsequently be explained in connection with FIG. 4. However, even though the technique described in connection with FIG. 4 may have particular advantages, other techniques can also be used in the prediction techniques of the present disclosure. Furthermore, the different data processing steps described in connection with the technique of FIG. 4 can also be applied in the other techniques for generating a prediction algorithm described above (unless they are specific to the particular technique of FIG. 4).

Figure 4:
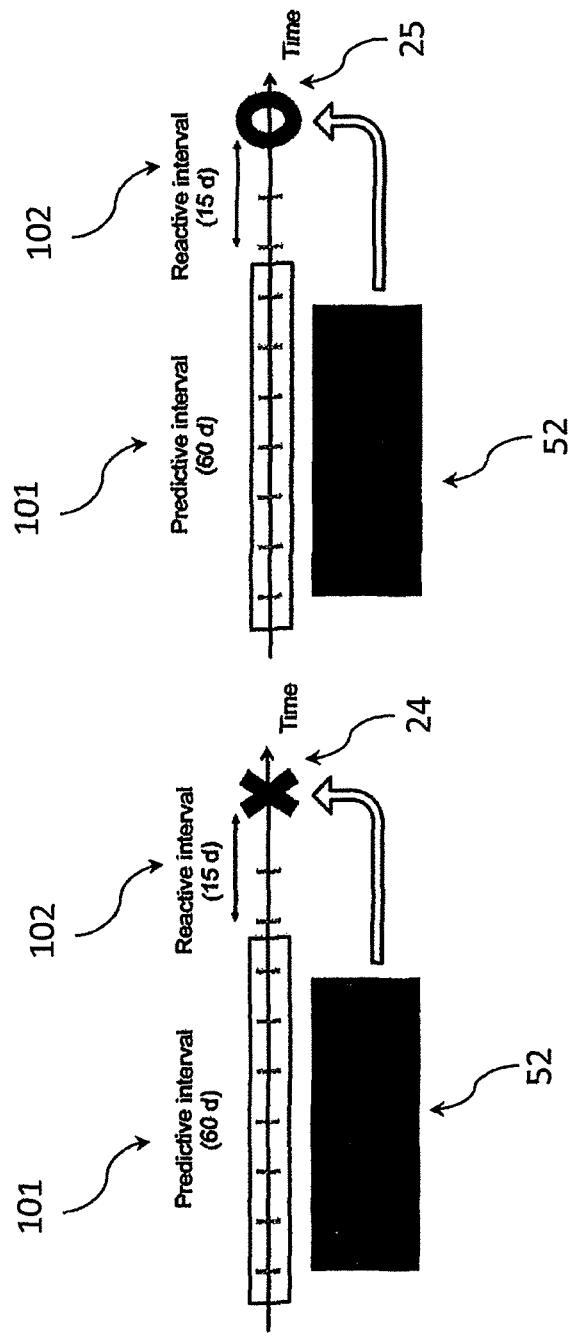
FIG. 4 illustrates different parameters and data used in the prediction algorithm according to an embodiment of the present disclosure.

In the example of FIG. 4, the predicting algorithm for predicting a failure state can be generated by solving a binary classification problem. Thus, the prediction algorithm can be configured to have a binary output, i.e., one output state indicating that a failure state is expected and a second output state indicating that no failure state is expected. In other words, the binary classification problem can include as binary event the presence or absence of a failure state occurring at a predetermined time.

In other examples, the classification problem can have more than two classes (e.g., three, four or more than four classes). For instance, the classification problem can involve four classes including a failure state requiring a visit, a failure state solvable by an operator of the automated analyzer, a failure state solvable by remote service and a state in which no service needed. Other failure states discussed above can additionally or alternatively form a class of the two or more classes of the classification problem.

As depicted in FIG. 4, the calibration data and/or quality control data 52 can be processed to train the prediction algorithm.

In one example, the calibration data and/or quality control data 52 can be averaged over a plurality of calibration routines and/or quality control routines to train the prediction algorithm. In this example, the averaged calibration data and/or quality control data can include a result of a plurality of different calibration routines and/or quality routines.

The calibration data and/or quality control data 52 can be averaged in one or more dimensions. In one example, the calibration data and/or quality control data 52 can be averaged over a predetermined period of time. In addition, or alternatively, calibration data and/or quality control data of different types can be averaged.

In one example, an automated analyzer may provide different functions for which calibration routines or quality control routines can be performed (e.g., a plurality of assays available on the automated analyzer). The calibration data and/or quality control data can include an average value over all calibration data and/or quality control data for the different functions of the automated analyzer or over a subset of the functions (e.g., an average value over all assays of an automated analyzer or a subset of the assays).

In some examples, the calibration data and/or quality control data can be processed before an average can be calculated. For instance, the calibration data and/or quality control data originating from different calibration routines or quality routines of the automated analyzer (e.g., of routines from different assays) can be normalized before averaging. In one example, the calibration data and/or quality control data can be used by employing average and variation values of the respective calibration data and/or quality control data. In this manner, data of different sources can be combined and used for generating and training the prediction algorithm.

In some examples, the calibration data and/or quality control data can be data of different data types (e.g., numeric or nominal data). The processing of the calibration data and/or quality control data of the different data types can include generating distribution information (e.g., average and/or variation information) for numeric calibration data and/or quality control data. In addition, or alternatively, the processing of the calibration data and/or quality control data can include determining frequency information used for nominal calibration data and/or quality control data.

For instance, the result of a quality control routine may indicate that a measurement result of the automated analyzer is within predetermined boundaries. In this example, the quality control data may be a nominal variable having two different states, i.e., "within boundaries" or "not within boundaries." In another example, the result of a quality control routine may include a concentration value for the concentration of the predetermined consequent in a quality control. In this example, the quality control data can include a numerical value (i.e., the concentration value).

In addition, or alternatively, the processing of the quality control and/or calibration data can include integrating or averaging the quality control data and/or calibration data over a predetermined period of time.

In still other examples, the quality control and/or calibration data can be associated with time bins of a predetermined duration. In addition, only a sample quality control and/or calibration data can be processed of each time bin (or an average value can be determined representing each time bin). In this manner, the calibration data and/or quality control data of different sources can be combined to generate or train the prediction algorithm. In addition, providing bins for the calibration data and/or quality control data can allow for dealing with events which occur with a changing frequency.

The example of FIG. 4 illustrates the calibration data and/or quality control data 52 as a matrix of color-coded data values. Each field can represent a parameter obtained in a particular calibration routine and/or quality routine. Naturally, this particular representation is purely illustrative and can be different in other examples when the techniques of the present disclosure are used.

In the example of FIG. 4, a predictive interval 101 (which will be explained in more detail below) can be split into a plurality of overlapping bins. All calibration data and/or quality control data used in the generation and training process of the prediction algorithm that falls within a certain bin can be combined to yield a combined value. In this manner, the different predictive intervals can have the same length which may facilitate the generation and training procedure of the prediction algorithm.

In addition, or alternatively, the quality control and/or calibration data or the data regarding the occurrence of failure states (or both) can be filtered before using them to generate and train the prediction algorithm. In one example, only a subset of the data available can be used to generate and train the prediction algorithm.

For example, the data regarding the occurrence of failure states may include a predetermined number of records of the occurrence of actual failure states (e.g., retrieved from service data of the automated analyzer). On the other hand, a number of negative events (i.e., 'normal' operation) may be considerably larger than a number of positive events (failures). In other words, most of the time the automated analyzer can be in a normal operating state. In view of that, the data sets regarding the occurrence of a failure state can be (fairly) imbalanced. Therefore, the data can be filtered to provide a (more) balanced dataset regarding to data points associated with failure states and data points associated with normal operation of the automated analyzer.

In one example, a filtering technique can include selecting one data set among a plurality of datasets associated with a point in time where no failure state occurred for each failure state included in the data set. For example, the dataset among the plurality of data sets that is associated with a point in time where no failure state occurred can be randomly sampled (e.g., a dataset of a point in time a predetermined period of time before the failure state).

After several aspects of the quality control and/or calibration data processing to generate and train the prediction algorithm have been discussed above, the following sections will include various details regarding the data sources of the quality control and/or calibration data used in the generation and training process.

In one example, the quality control and/or calibration data can be obtained from one or more automated analyzers which share a predetermined characteristic with the automated analyzer on which the prediction algorithm can be applied.

For example, the one or more automated analyzers whose calibration data and/or quality control data can be used to generate and train the prediction algorithm can be of the same type as the automated analyzer on which the prediction algorithm is to be applied (e.g., automated analyzers of the same model or the same product family as the automated analyzer on which the prediction algorithm is to be applied).

In other examples, the one or more automated analyzers whose calibration data and/or quality control data can be used to generate and train the prediction algorithm can share a predetermined component or group of components with the automated analyzer on which the prediction algorithm is to be applied. For example, two different types of automated analyzers may include the same detection module for analyzing samples.

In still other examples, the one or more automated analyzers whose calibration data and/or quality control data can be used to generate and train the prediction algorithm can share a predetermined functionality or group of functionalities with the automated analyzer on which the prediction algorithm is to be applied. For example, the automated analyzers may share a particular assay that can be performed by the automated analyzer, or a group of assays.

In general, as can be seen, the automated analyzers used in the generation and training phase may have some similarities with the automated analyzer on which the prediction algorithm is to be applied.

In one example, the automated analyzer on which the prediction algorithm is to be applied can be used in the generation and training phase of the prediction algorithm (or the automated analyzer can be one of the automated analyzers used in the phase). However, in other examples, the automated analyzer on which the prediction algorithm is to be applied may not be part of the group of analyzers whose calibration data and/or quality control data is used for generating and craning the prediction algorithm.

In addition, or alternatively, the generation and training phase of the prediction algorithm can include setting one or more parameters of the prediction algorithm. As depicted in FIG. 4, one parameter of the prediction algorithm can be a reactive interval 102. The reactive interval can be a period of time separating the time at which the calibration data and/or quality control data used for prediction are collected and the time of the failure state is to be predicted. The length of the reactive interval 102 can be important to leave enough time to initiate countermeasures to prevent the failure state or avoid severe consequence of the failure state.

Thus, generating the predicting algorithm can include determining a length of a reactive interval 102 between a period of time in which the quality control and/or calibration data is used to predict a failure event and the failure event.

However, in other examples, a reactive interval may be obtained from the application of the prediction algorithm (e.g., a certain failure state may be predictable from the calibration data and/or the quality control data with a certain reactive interval). In these examples, the reactive interval may be part of the prediction of the prediction algorithm.

Moreover, as depicted in FIG. 4, generating the predicting algorithm can include defining a predictive interval 101 whose quality control and/or calibration data can be used to predict a failure event of the automated analyzer. In addition, the predictive interval can be split into a plurality of sub-intervals and wherein quality control and/or calibration data within each sub-interval can be integrated (e.g., as discussed above).

In general, the length of the predictive interval and/or the number of sub-intervals can be selected to fulfill one or more of the following objectives. On the one hand, the length of the predictive interval and/or the number of sub-intervals can be selected so that the predictive power of the prediction algorithm is improved. For instance, a longer predictive interval may reduce a number of false alerts. However, a longer predictive interval may also reduce a sensitivity of the prediction algorithm. In the example of FIG. 4, the predictive interval can be set to 60 days. However, this length is merely illustrative and can be different in other examples the techniques of the present disclosure are employed.

In connection with FIG. 3 and FIG. 4, different techniques to process the calibration data and/or quality control data have been discussed. As can be seen when considering the diagram of FIG. 1, in the actual prediction phase, the prediction algorithm quality control and/or calibration data can be used in a similar manner as in the generation and training phase. The data processing techniques described above in connection with the generation and training phase can thus be equally applied in the prediction phase when the trained prediction algorithm is applied to predict a failure state of the automated analyzer (unless the respective processing technique is specific to the training phase). For example, calibration data and/or quality control data can be averaged, normalized, and combined in the same manner as described above in connection with the training phase in the prediction phase.

In one example, the predictive interval 101 determined in the generation and training phase can also be used in the prediction phase. In other examples, a length of the predictive interval 101 may be different in the training phase and the prediction phase.

Figure 5:
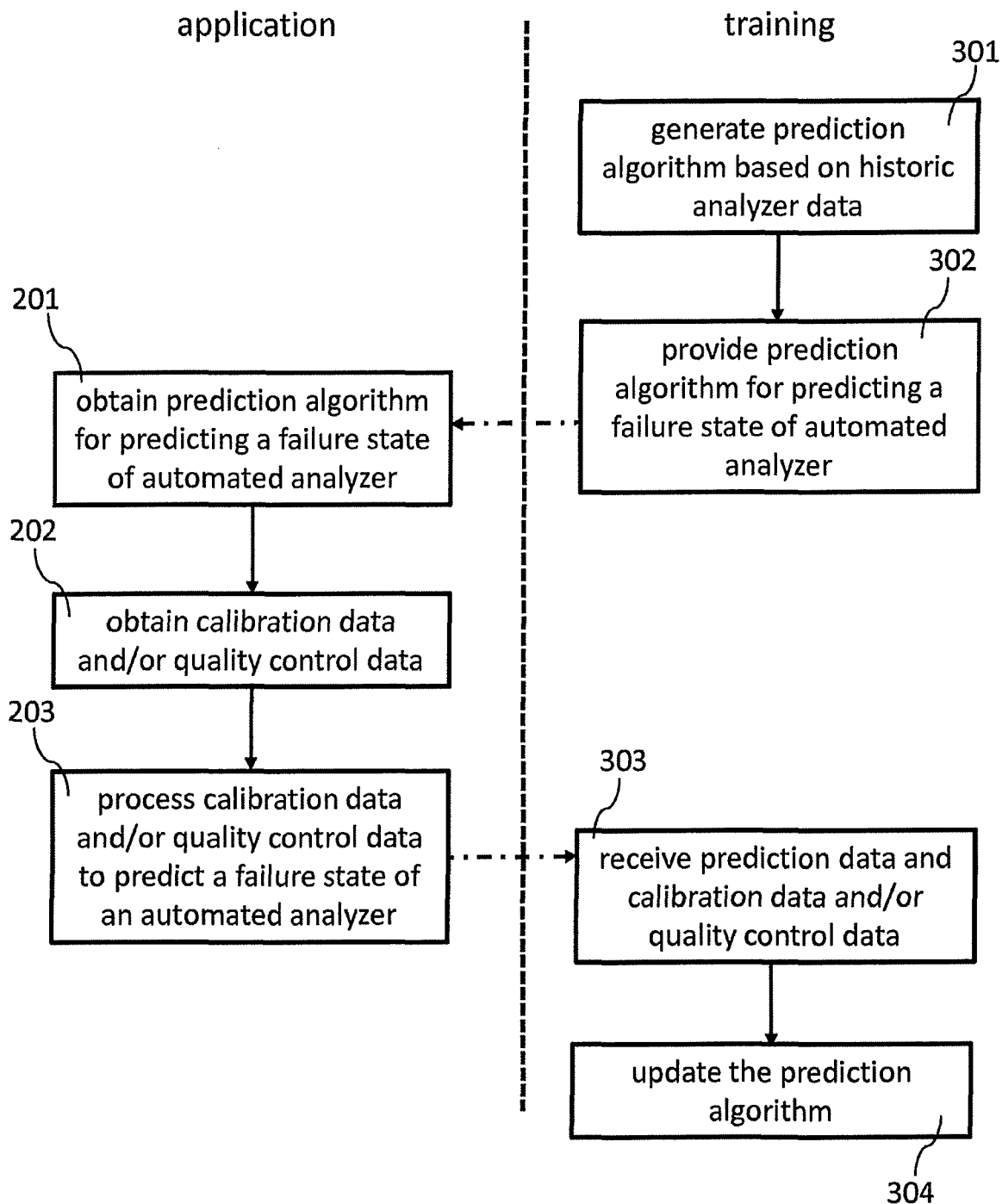
FIG. 5 illustrates a flow diagram of different methods according to an embodiment of the present disclosure.

Coming back to FIG. 1 and FIG. 5, it can be seen that the prediction algorithm 1 can be updated 303, 304 in some examples of the present disclosure. For instance, data regarding the occurrence of failure states 7, 8 can be used 15, 16 to update the prediction algorithm during operation of the automated analyzer.

In one example, at some point in time, a service technician 4 may have to attend to the automated analyzer 2. The service data 7 obtained from this visit can be used to update the prediction algorithm 1 applied in the automated analyzer 2. In general, the update procedure can include the same operations as described above in connection with FIG. 3 and FIG. 4 concerning the training and generation face of the prediction algorithm.

In some examples, the prediction algorithm 1 can be continuously updated during operation of the automated analyzer. In some examples, as depicted in FIG. 1, data regarding the occurrence of failure states of the automated analyzer 2 on which the prediction algorithm 1 is applied used to update the prediction algorithm 1. In addition, or alternatively, data obtained from other automated analyzers (e.g., automated analyzers sharing a predetermined characteristic with the automated analyzer 2 on which the prediction algorithm 1 is applied) can be used to update the prediction algorithm 1.

In one example, an updated prediction algorithm can be provided to the automated analyzer 2 in regular intervals or upon occurrence of certain trigger elements from a remote location.

Example Prediction Technique

In the preceding sections, different aspects of generating and training the prediction algorithm and applying the prediction algorithm in an automated analyzer to predict a failure state of the automated analyzer have been discussed. Subsequently, in connection with FIGS. 6a-b, a concrete example of an application of the techniques of the present disclosure and experimental and results evaluating this application will be discussed. The specific aspects of this particular application case are stated for illustrative purposes only. As discussed in the remaining disclosure, the techniques of the present disclosure can also be applied differently in other examples. However, different aspects of the concrete example discussed below can also be applied in combination with some of the techniques described in the other passages of the present disclosure.

Figure 6A:
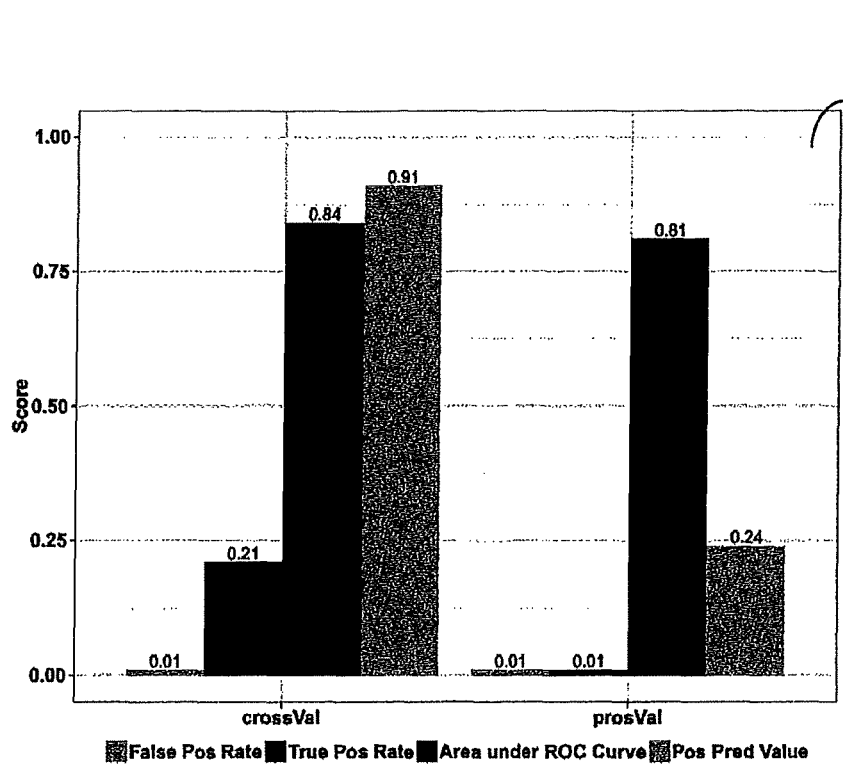
FIGS. 6a-b illustrate experimental data retrieved by using the technique according to an embodiment of the present disclosure.
Figure 6B:
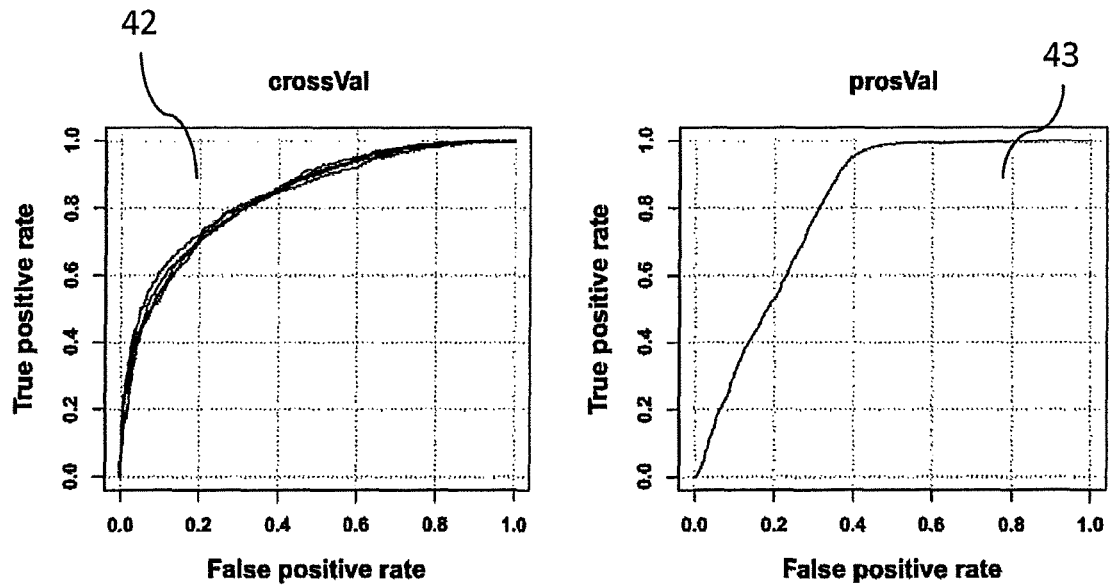

In the example of FIGS. 6a-b, the problem of generating a prediction algorithm has been formulated as a binary classification problem, where each instance for initial training can be endowed a target label that is such binary event at each time point as the presence/absence of an emergency service visit.

One way to label the events is as follows: the dates marked with emergency service visits are tagged positive and any date without a visit in record is recognized as a negative event. However, despite the fact that there is no record until a service visit takes place, instruments are supposed to be running under unstable condition just a few days before the visit, which can confuse and impair the training procedure. Unexpected failures are usually rare and the size of opposing classes can be imbalanced, which might lead to problems for learning algorithms (ratio of the number of no-visit days to emergency service events is over 1000 for the dataset used in the illustrative example).

In order to account for abnormal performance under unstable condition and balance the training data, positive instances, denoted by y=+1, include all true records of emergency service visit in the service data as well as the two time bins (defined in the following paragraphs) prior to a visit. Negative instances, denoted by y=−1 on the other hand, are randomly sampled from dates that are at least 7 days away from any service visit.

In order to have a balanced training set, the number of randomly sampled negative instances can be chosen so that it is comparable to the number of positive instances.

The calibration data and quality control data used in the illustrative example of FIGS. 6a-b will be discussed next. Calibration data and quality control data can comprise of thousands of operation records for each automated analyzer, and each record can be detailed specific to one operation performed at a specific time. It can be difficult to analyze these records due to several characteristics. First, operation details can be documented by a number of mixed type of attributes (either categorical or numeric). Second, the data are non-equidistant temporal series, meaning that notably each operation record can be endowed with a time stamp indicating the performance time but different operations are not necessarily performed at equidistant time intervals. Third, the data the operation data can be noisy in the sense that an operator sometimes makes personal mistakes which do not represent true condition of the underlying instrument.

In the example of FIGS. 6a-b, the calibration data and quality control data can be preprocessed by integrating records present over certain time periods, and extract predictive features for a positive instance in the following way.

A reactive interval of 15 days ahead of a positive instance is selected (simulating reaction-to-alert time period right before a failure state, e.g., an unexpected instrument breakdown, and pool all calibration and quality control records within a predictive interval of [−60, −1] days, i.e., 60 days to 1 day prior to the start of the reactive interval.

In the example of FIGS. 6a-b, D monitoring attributes have been selected and, for each attribute, data from the 60-day predictive interval are combined into B variables by computing the frequency for categorical attributes and the mean and variance for numeric attributes. Specifically, the predictive interval [−60, −1] is cut into bins of uniform size so that neighboring bins are overlapped by half the size side by side. The bin size for calibration data is chosen as 14 days so that BCal=7 bins are formed in the illustrative example, denoted by [−56, −43], [−49, −36], [−42, −29], . . . , [−14, −1], and DCal=11 related attributes are under inspection in our study; the bin size for quality control data is chosen as 6 days so that BQC=19 bins are formed, denoted by [−60, −55], . . . , [−6, −1], and DQC=3 related attributes are considered in our study. Finally, in total a list of P=BCal×DCal+BQC×DQC=134 predictive variables can be obtained, denoted by a feature vector x∈RP.

Notably, the negative instances can be treated in the same way even though no alert is received. If no calibration or quality control operation is reported in some bin for an instance, the corresponding feature value can be imputed (before fitting a learning algorithm) by the median value of the other observed instances.

The generation of the prediction algorithm will be discussed next. The data to fit a learning algorithm is D={(xi, yi)}Ni=1, where N denotes the total number of instances collected from different instruments and at different dates. Each instance can comprise of yi∈{+1, −1}, the target label of binary event representing the presence/absence of emergency service visit, and xi ∈RP, a list of feature variables depicting the behaviors of the instrument performance prior to an event. Given D, the goal is to obtain a classifier that correctly labels instances with unseen outcome.

In the example of FIGS. 6a-b, a Random Forests algorithm as proposed by Breiman (in *Machine learning*, 45(1): 5-32, 2001) can be selected to solve the classification problem. A series of classification trees can be built using different subsets of training data and each tree can predict a label for an unseen instance individually. The forest can predict the probability of an instance being positive by the percentage of positive predictions from individual trees, which can be a number between 0 and 1 quantifying the belief that an instrument should call for an emergency service visit. Finally, a discrimination threshold can be determined beforehand and the forest can label an instance to be positive if the predicted probability exceeds the threshold. Since there are only two possible outcomes, the discrimination threshold is ordinarily selected as 0.5 hereinafter unless otherwise specified.

In practice, the learning algorithm can be inherited from the R implementation randomForest (proposed by Liaw and Wiener in "Classification and regression by randomforest," R news, 2(3):18-22, 2002) with built-in default parameters.

The results of the evaluation of the prediction algorithm will be discussed in the subsequent passages. A predictive model built from the learning algorithm can be evaluated with historical data before real-world deployment. The dataset D can be split into two parts, one for training a model and the other for testing the predictive performance of the model by calculating evaluation scores as criteria. The scores of particular interest are:

False Positive Rate (FPR): The number of predicted emergency service visits for which maintenance is not required at a specific discrimination threshold setting divided by the total number of no-visit events, i.e., FPR=FP/(FP+TN). It can be particularly interesting that a desirable model can make prediction with low FPR in order to pay less for unnecessary visits.

True Positive Rate (TPR): The number of predicted emergency service visits for which maintenance is indeed required at a specific discrimination threshold setting divided by the total number of emergency service visits, i.e., TPR=TP/(TP+FN). The higher the TPR is, the more sensitive the learning model is to detect pending failures.

Area under Receiver Operating Characteristic Curve (AUROC): The area under the ROC curve plotting TPR against FPR at various discrimination threshold settings. Since it is common to trade-off between TPR and FPR in decision-making according to business need, AUROC is a good indicator of model performance in general. The score is a number between 0 and 1, and the larger the score is, the more effective the model can be to adjust the trade-off.

Positive Predictive Value (PPV): The number of predicted emergency service visits for which maintenance is not required at a specific discrimination threshold setting divided by the total number of predicted emergency service visits, i.e., PPV=TP/(TP+FP). PPV underlies how many positive alarms raised by the prognostic algorithm are true alerts. By PPV, we are aware of how much a prognostic model has to sacrifice by admitting more positive predictions in order to achieve certain level of precision of detected true failures. Two evaluation approaches adopted in this study are:

k-fold cross-validation (crossVal): the entire dataset D is randomly divided into k disjoint subsets, called "folds", of approximately equal size (regardless of the time factor as opposed to the second approach below). Each fold is used as a test set against which a model trained on the other folds is evaluated, and the evaluation scores calculated against all folds are averaged as a final score.

Prospective hold-out validation (prosVal): a time point T is first determined and the entire dataset D is divided into two parts according to the time stamp of each event. A model is trained on data before T and validated against data after T by calculating the evaluation scores. This approach only considers to predict for succeeding events based on previously observed data, which is the case in real-world application.

The capability of predicting emergency service visit from calibration data and quality control data can be estimated. For this purpose, data which has been collected from a large fleet of clinical analyzers over several years can be employed.

For 5-fold cross-validation, a total of 3139 positive and 7034 negative instances were pooled, 20% of which are randomly held out for testing at each fold. For prospective hold-out validation, a training set consisting of 2014 positive and 5702 negative instances were pooled and an independent test set consisting of 1383 positive and 3342 negative instances. Confusion matrices for both validation approaches are summarized in Table 1.

TABLE 1

| crossVal | Actual Neg | Actual Pos | prosVal | Actual Neg | Actual Pos |
|---|---|---|---|---|---|
| Pred Neg | 1394 | 497 | Pred Neg | 3326 | 1378 |
| Pred Pos | 13 | 131 | Pred Pos | 16 | 5 |

As shown in FIG. 6a, an AUROC score greater than 0.8 is achieved for both cross-validation and prospective hold-out validation, which firmly supports the motivation of this study that calibration and quality control performance can be a significant indicator of instrument condition and positively demonstrates that predicting emergency service visits from calibration and quality control data with machine learning methods can be particularly viable. Results with cross-validation approach show that, while maintaining only 1% of false alarms, 21% of emergency service calls can be detected in advance by (at least) 15 days, and 91% of positive alarms raised are indeed true ones. In fact, this length of reaction-to-alert period can be further tuned to adjust a better trade-off between prediction accuracy and business value. On the other hand, with prospective hold-out validation approach where a predictive model is always trained on past data and validated against future data, results show that only 1% of true service calls can be detected at a tolerance of 1% of false alarms, and only 24% of positive alarms are true concerns.

The ROC curve in FIG. 6b, indicates that we can achieve approximately 25% of true positive alerts by adjusting the discrimination threshold and admitting loosely 10% of false calls.

The reason for the difference between the two validation approaches is probably that calibration and quality control data from the past can be inconsistent with future data. The production of chemical reagents, calibrators and control materials vary in time, and it can be difficult to characterize the performance pattern of a new batch by analyzing earlier batches. While cross-validation avoids the heterogeneous representation of data by shuffling the instances along time for training and testing, in case of prospective validation we are only able to identify more failures in advance of instrument breakdown by inevitably allowing certain amount of false alarms.

ADDITIONAL ASPECTS

In the preceding detailed description multiple examples of systems and methods for predicting a state of an automated analyzer have been discussed. However, the systems and methods for predicting a state of an automated analyzer can also be configured as set out in the following:

A method for predicting a failure state of an automated analyzer for analyzing a biological sample is presented. The method can comprise obtaining a prediction algorithm for predicting a failure state of an automated analyzer. The prediction algorithm can be configured to predict a failure state of the automated analyzer based on calibration data and/or quality control data generated by an automated analyzer. The method can also comprise obtaining calibration data and/or quality control data of the automated analyzer and processing the calibration data and/or quality control data by using the prediction algorithm to predict a failure state of the automated analyzer.

The method can also comprise generating the prediction algorithm based on historic analyzer data. The historic analyzer data can include historic data retrieved from a plurality of automated analyzers sharing one or more characteristics with the automated analyzer. The historic data can include historic data retrieved from the automated analyzer. The historic data can include historic data regarding the occurrence of failure states and historic calibration data and/or quality control data. The historic data regarding the occurrence of failure states can include service data of automated analyzers. The service data can include data retrieved from reports by a technician. The service data can include one or more of an automated analyzer ID, a visit date of a service technician, component consumption information and descriptions of the activities performed on the automated analyzer. The historic data regarding the occurrence of failure states can include information regarding errors generated by an automated analyzer.

The historic calibration data and/or quality control data can include frequency data of calibration events or quality control events. The historic calibration data and/or quality control data can include distribution information (e.g., average values and/or variation values) of signals measured during calibration events or quality control events. The historic calibration data and/or quality control data can include data regarding changes of signals measured during calibration events or quality control events. The historic calibration data and/or quality control data can include data regarding one or more of a calibration frequency, calibration curve slopes and intercepts, ratios of current calibration slopes to previous ones, signal variations of calibrated duplicate measurements, quality control frequency, and ratios of measured quality control concentration to quality control target value concentrations and variations thereof.

The method can further comprise finding a relationship between the historic data regarding the occurrence of failure states and the historic calibration data and/or quality control data to generate the prediction algorithm. The finding a relationship can include correlating the historic data regarding the occurrence of failure states and the historic calibration data and/or quality control data. The finding a relationship can include using a classification technique on the historic data regarding the occurrence of failure states and the historic calibration data and/or quality control data to find the relationship. The classification technique can include one or more of a technique including using technique using a support vector machine, a random forest machine learning algorithm, a deep learning algorithm, a logistic regression technique, a (naïve) Bayes technique, a gradient boosting technique or linear discriminant analysis.

The method can further comprise solving a binary classification problem to generate the prediction algorithm.

The method can further comprise solving a classification problem with more than two classes to generate the prediction algorithm. The binary classification problem can include, as binary event, the presence or absence of a failure state occurring at a predetermined time. The failure state can be one of: a failure state requiring an emergency service with a visit at the automated analyzer, a failure state requiring an intervention by the operator of the automated analyzer, or a failure of a component of the automated analyzer.

The method can further comprise averaging the calibration data and/or quality control data over a plurality of assays available on the automated analyzer to generate the prediction algorithm. The calibration data and/or quality control data of different assays can be normalized before averaging.

The method can further comprise calculating distribution information (e.g., average or variation information) for numeric calibration data and/or quality control data and generating the prediction algorithm based on the calculated data.

The generation of the prediction algorithm calibration data and/or quality control data can be integrated over a predetermined period of time. The generating of the predicting algorithm can include determining the length of a predetermined reactive interval between a period of time in which the quality control and/or calibration data can be used to predict a failure event and the failure event. The generating of the predicting algorithm can include defining a predictive interval whose quality control and/or calibration data can be used to predict a failure event of the automated analyzer. The predictive interval can be split into a plurality of sub-intervals. Quality control and/or calibration data within each sub-interval can be integrated.

The calibration data and/or quality control data can include data as defined for the historical calibration data and/or quality control data as above.

The method as described above to process the historic calibration data and/or quality control data can be used in the step of processing the calibration data and/or quality control data by using the prediction algorithm to predict a failure state of an automated analyzer.

The automated analyzer can be an in-vitro analyzer.

A quality control data can be a liquid formulation including a predefined quantity of one or more substances.

Calibration data can include data from measurements in which a response signal to one or more standard calibrators having a known composition can be determined by the analyzer to generate a relationship between the response signal and the known composition.

Quality control data can include data obtained when testing one or more control materials with known target measurement values to be output by the analyzer to check that the automated analyzer operates within a predetermined limit of accuracy.

The method can further comprise determining of a response signal of the automated analyzer to one or more standard calibrators having a known composition, generate a relationship between the response signal and the known composition, and including the relationship into the calibration data.

The method can further comprise determining of a response signal of the automated analyzer to one or more one or more control materials with known target measurement values, checking that the automated analyzer operates within a predetermined limit of accuracy and/or precision, and including results of the checking step in the quality control data.

The method can further comprise updating the prediction algorithm by using additional calibration data and/or quality control data and data regarding the occurrence of failure states, and obtaining an updated prediction algorithm at the automated analyzer. The update operation can be carried out regularly or continuously.

The method can further comprise outputting an indicator that a failure state is likely to occur. Outputting an indicator that a failure state is likely to occur can include generating a warning message for an operator of the automated analyzer. Outputting an indicator that a failure state is likely to occur can include generating a warning message for remote service personnel of the automated analyzer.

The predicting algorithm for predicting a failure state of the analyzer does not process any data from sensors dedicated to predict a failure state.

The method can further comprise collecting the data regarding the states of a plurality of automated analyzers and generating the predicting algorithm for predicting a failure state of an automated analyzer based on the data regarding the states of a plurality of automated analyzers.

The predicting algorithm for predicting a failure state of an automated analyzer can be generated based on data regarding the states of a plurality of automated analyzers which share a predetermined number of characteristics with the automated analyzer whose failure state is to be predicted.

The method can be a computer-implemented method.

A computer-readable medium having instructions stored thereon which when carried out on a computer system make the computer system perform the above methods is presented.

An automated analyzer for analyzing a biological sample is presented. The automated analyzer can comprise a detection unit to detect one or more properties of a sample, memory having instructions stored thereon which when carried out on a computer system make the computer system perform the above methods, and a processor configured to carry out the instructions stored in the memory.

Computer-Implementation

Further disclosed and proposed is a computer program including computer-executable instructions for performing the method according to the present disclosure in one or more of the embodiments enclosed herein when the program is executed on a computer or computer network. Specifically, the computer program may be stored on a computer-readable data carrier. Thus, specifically, one, more than one or even all of method steps as disclosed herein may be performed by using a computer or a computer network, preferably by using a computer program.

Further disclosed and proposed is a computer program product having program code, in order to perform the method according to the present disclosure in one or more of the embodiments enclosed herein when the program is executed on a computer or computer network. Specifically, the program code may be stored on a computer-readable data carrier.

Further disclosed and proposed is a data carrier having a data structure stored thereon, which, after loading into a computer or computer network, such as into a working memory or main memory of the computer or computer network, may execute the method according to one or more of the embodiments disclosed herein.

Further disclosed and proposed is a computer program product with program code stored on a machine-readable carrier, in order to perform the method according to one or more of the embodiments disclosed herein, when the program is executed on a computer or computer network. As used herein, a computer program product refers to the program as a tradable product. The product may generally exist in an arbitrary format, such as in a paper format, or on a computer-readable data carrier. Specifically, the computer program product may be distributed over a data network.

Further disclosed and proposed is a modulated data signal which contains instructions readable by a computer system or computer network, for performing the method according to one or more of the embodiments disclosed herein.

Referring to the computer-implemented aspects of the present disclosure, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing measurements.

Further disclosed and proposed is a computer or computer network comprising at least one processor, wherein the processor is adapted to perform the method according to one of the embodiments described in this description.

Further disclosed and proposed is a computer loadable data structure that is adapted to perform the method according to one of the embodiments described in this description while the data structure is being executed on a computer.

Further disclosed and proposed is a storage medium, wherein a data structure is stored on the storage medium and wherein the data structure is adapted to perform the method according to one of the embodiments described in this description after having been loaded into a main and/or working storage of a computer or of a computer network.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A computer-implemented method for predicting a failure state of an automated analyzer for analyzing a biological sample, the method comprising:
   a determining, by the automated analyzer, a machine learning prediction algorithm for predicting a failure state of an automated analyzer based on historic analyzer data, wherein the historic analyzer data includes historic data regarding the occurrence of failure states and historic calibration data and/or quality control data, and wherein the machine learning prediction algorithm is configured to predict a failure state of the automated analyzer based on calibration data and/or quality control data generated by an automated analyzer;
   obtaining, by the automated analyzer, calibration data and/or quality control data of the automated analyzer; and
   processing, by the automated analyzer, the calibration data and/or quality control data by using the machine learning prediction algorithm to autonomously predict a failure state of the automated analyzer,
   wherein determining, by the automated analyzer, the machine learning prediction algorithm includes training an initial machine learning prediction algorithm using the historic data regarding the occurrence of failure states and the historic calibration data and/or quality control data,
   wherein the machine learning prediction algorithm is configured to have one output state indicating that a failure state is expected and a second output state indicating that no failure state is expected,
   wherein determining, by the automated analyzer, the machine learning prediction algorithm comprises determining a length of a reactive interval between a period of time in which the quality control and/or the calibration data is used to predict a failure event and the failure event.

2. The computer-implemented method of claim 1, wherein the historic analyzer data includes historic data retrieved from a plurality of automated analyzers sharing one or more characteristics with the automated analyzer.

3. The computer-implemented method of claim 2, wherein the historic data regarding the occurrence of failure states includes service data of the plurality of automated analyzers.

4. The computer-implemented method of claim 1, further comprising finding, by the automated analyzer, a relationship between the historic data regarding the occurrence of failure states and the historic calibration data and/or quality control data to determine the machine learning prediction algorithm.

5. The computer-implemented method of claim 4, further comprising:
   classifying, by the automated analyzer, the historic data regarding the occurrence of failure states by a classification technique; and
   determining, by the automated analyzer, a relationship between the historic calibration data and/or quality control data.

6. The computer-implemented method of claim 1, further comprising solving, by the automated analyzer, a binary classification problem to determine the machine learning prediction algorithm.

7. The computer-implemented method of claim 6, wherein the failure state is one of: a failure state requiring an emergency service with a visit at the automated analyzer, a failure state requiring an intervention by an operator of the automated analyzer, or a failure of a component of the automated analyzer.

8. The computer-implemented method of claim 1, further comprising averaging, by the automated analyzer, the calibration data and/or quality control data over a plurality of assays available on the automated analyzer to determine the machine learning prediction algorithm.

9. The computer-implemented method of claim 1, further comprising:
calculating, by the automated analyzer, distribution information for numeric calibration data and/or quality control data; and
generating, by the automated analyzer, the machine learning prediction algorithm based on the calculated data.

10. The computer-implemented methods of claim 1, further comprising:
calculating, by the automated analyzer, frequency information for categorical calibration data and/or quality control data; and
generating, by the automated analyzer, the machine learning prediction algorithm based on the calculated data.

11. The computer-implemented method of claim 1, further comprising:
determining a response signal of the automated analyzer to one or more standard calibrators having a known composition;
generating, by the automated analyzer, a relationship between the response signal and the known composition; and
including, by the automated analyzer, the relationship into the calibration data.

12. The computer-implemented method of claim 1, further comprising:
determining, by the automated analyzer, a response signal of the automated analyzer to one or more one or more control materials with known target measurement values;
checking, by the automated analyzer, that the automated analyzer operates within a predetermined limit of accuracy and/or precision; and
including, by the automated analyzer, results of the checking step in the quality control data.

13. The computer-implemented method of claim 1, further comprising continuously updating, by the automated analyzer, the machine learning prediction algorithm based on newly received calibration data and/or quality control data of the automated analyzer during operation of the automated analyzer.

14. The computer-implemented method of claim 1, wherein determining the machine learning prediction algorithm comprises determining a machine learning prediction algorithm installed on the automated analyzer.

15. An automated analyzer for analyzing a biological sample, the automated analyzer comprising:
a detection unit to detect one or more properties of the biological sample;
a processor; and
a memory comprising a plurality of instructions stored thereon that, in response to execution by the processor, causes the automated analyzer to:
determine a machine learning prediction algorithm for predicting a failure state of an automated analyzer based on historic analyzer data, wherein the historic analyzer data includes historic data regarding the occurrence of failure states and historic calibration data and/or quality control data, and wherein the machine learning prediction algorithm is configured to predict a failure state of the automated analyzer based on calibration data and/or quality control data generated by an automated analyzer;
obtain calibration data and/or quality control data of the automated analyzer; and
process the calibration data and/or quality control data by using the machine learning prediction algorithm to autonomously predict a failure state of the automated analyzer,
wherein to determine the machine learning prediction algorithm includes to train an initial machine learning prediction algorithm using the historic data regarding the occurrence of failure states and the historic calibration data and/or quality control data,
wherein the machine learning prediction algorithm is configured to have one output state indicating that a failure state is expected and a second output state indicating that no failure state is expected,
wherein to determine the machine learning prediction algorithm further includes to determine a length of a reactive interval between a period of time in which the quality control and/or the calibration data is used to predict a failure event and the failure event.

16. The automated analyzer of claim 15, wherein the plurality of instructions further causes the automated analyzer to:
find a relationship between the historic data regarding the occurrence of failure states and the historic calibration data and/or quality control data to determine the machine learning prediction algorithm;
classify the historic data regarding the occurrence of failure states by a classification technique; and
determine a relationship between the historic calibration data and/or quality control data.

17. The automated analyzer of claim 15, wherein the failure state is one of: a failure state requiring an emergency service with a visit at the automated analyzer, a failure state requiring an intervention by an operator of the automated analyzer, or a failure of a component of the automated analyzer.

18. The automated analyzer of claim 15, wherein the memory further comprises the machine learning prediction algorithm installed thereon; and
wherein to determine the machine learning prediction algorithm comprises to determine the machine learning prediction algorithm installed on the automated analyzer.

19. The automated analyzer of claim 15, wherein the plurality of instructions further causes the automated analyzer to continuously update the machine learning prediction algorithm based on newly received calibration data and/or quality control data of the automated analyzer during operation of the automated analyzer.

20. One or more non-transitory machine-readable storage media comprising a plurality of instructions stored therein that, in response to execution by a processor, causes an automated analyzer to:
determine a machine learning prediction algorithm for predicting a failure state of an automated analyzer based on historic analyzer data, wherein the historic analyzer data includes historic data regarding the occurrence of failure states and historic calibration data and/or quality control data, and wherein the machine learning prediction algorithm is configured to predict a failure state of the automated analyzer based on calibration data and/or quality control data generated by an automated analyzer;

obtain calibration data and/or quality control data of the automated analyzer; and process the calibration data and/or quality control data by using the machine learning prediction algorithm to autonomously predict a failure state of the automated analyzer, wherein to determine the machine learning prediction algorithm includes to train an initial machine learning prediction algorithm using the historic data regarding the occurrence of failure states and the historic calibration data and/or quality control data, wherein the machine learning prediction algorithm is configured to have one output state indicating that a failure state is expected and a second output state indicating that no failure state is expected, wherein to determine the machine learning prediction algorithm further includes to determine a length of a reactive interval between a period of time in which the quality control and/or the calibration data is used to predict a failure event and the failure event.

* * * * *